United States Patent [19]

Poplawski

[11] Patent Number: 5,320,590

[45] Date of Patent: Jun. 14, 1994

[54] ORTHOPEDIC BRACING MECHANISM FOR FACILITATING HIP RECIPROCATION

[76] Inventor: Christopher Poplawski, 3600 Haven Ave. #1, Redwood City, Calif. 94063

[21] Appl. No.: 991,281

[22] Filed: Dec. 15, 1992

[51] Int. Cl.$^5$ ............................................. A63B 23/04
[52] U.S. Cl. ........................................ 602/5; 482/51
[58] Field of Search ...... 128/25 R, 25 B, 121.1–126.1, 128/103.1, 99.1; 602/5–7, 19, 23, 24, 39, 40; 482/74, 51

[56] References Cited

U.S. PATENT DOCUMENTS

| | | | |
|---|---|---|---|
| 62,982 | 3/1867 | Tucker | 602/19 |
| 3,095,875 | 7/1963 | Davidson et al. | 602/19 |
| 4,263,901 | 4/1981 | Nichols | 602/24 |
| 4,497,315 | 2/1985 | Fettweis et al. | 602/19 |
| 4,697,808 | 10/1987 | Larson et al. | 482/51 |
| 4,946,156 | 8/1990 | Hart | 272/70 |
| 4,964,628 | 10/1990 | Poplawski | 482/51 |

FOREIGN PATENT DOCUMENTS

| | | | |
|---|---|---|---|
| 2618325 | 1/1989 | France | 602/19 |
| 0820855 | 4/1981 | U.S.S.R. | 482/74 |

Primary Examiner—Robert A. Hafer
Assistant Examiner—Brian E. Hanlon

[57] ABSTRACT

An orthopedic bracing device worn around the posterior pelvic area of a person suffering from severe lower extremity weakness such as found with certain spinal cord injuries resulting in paraplegia. Children born with Spina Bifida who are paraplegics are also potential users of this type of brace. This device is a mechanism whereby the user is forced to extend one hip joint backwards when the other hip joint is flexed forward, thus generating the normal walking pattern of reciprocation. The mechanism consists of two pivot bars with their pivot point located equidistant from the center of the pelvic band. Two lever arms extend from each pivot point. The longer lever arm curves around towards the mechanical hip joint of the brace and attaches through a semi-rigid linkage system. The shorter lever arm extends downwards and attaches to an adjustable connecter bar. The connecter bar joins the two identical pivot bars. As one leg steps forward, forces are transferred through the mechanism forcing the other leg to extend backwards.

2 Claims, 2 Drawing Sheets

ORTHOPEDIC BRACING MECHANISM FOR FACILITATING HIP RECIPROCATION

FIELD OF INVENTION

The present invention relates to externally worn orthopedic appliances for facilitating walking and standing by persons with severe lower extremity weakness and particularly to apparatus designed to coordinate the reciprocal flexion and extension of the hip joints during walking.

CROSS-REFERENCE TO RELATED APPLICATION

This application is related to application Ser. No. 375,210 filed Jun. 30, 1989, now U.S. Pat. No. 4,964,628, granted Oct. 23, 1990.

DISCUSSION OF PRIOR ART

Heretofore, the mobility of the paraplegic person was accomplished with the assistance of numerous devices, all designed to provide stability and limited mobility to the weakened joints of the lower extremity. These devices all try to maximize stability and allow reciprocation with the least amount of friction, bulk and weight. The "LSU Reciprocating Gait Orthosis" by Durr-Fillauer Medical, Inc. of Chattanooga, Tenn. was the system of choice for many years. The disadvantages of the above-mentioned system revolve around the cable mechanism. Substantial friction is generated as the cables slip back and forth through their housings. Another disadvantage of the cable system is its requirement for high maintenance. Alignment between the cables and their attachment to the hip joints must be pro-fessionally maintained to prevent increased friction and eventual breakage. The required lubrication of the cables within their housings can create oily residues that are unsightly and difficult to clean.

The hip-reciprocating device in U.S. Pat. No. 4,964,628 to Poplawski, 1990 Oct. 23 reduces the friction dramatically by eliminating the cables. Although a vast improvement over the cable system, my previous invention has its own share of disadvantages. On larger users of this device, the bulk and weight of the materials used must be increased substantially to tolerate the tremendous torque created between the center pivot point and the ends of the pivot bar. This added mass increases the weight and bulk of the device. The user, already weakened by their disability, finds thier mobility further restricted by the weight of the device.

Users of this type of brace often use wheelchairs in conjuction with their brace. With the centrally located pivot point, there is a substantial increase in bulk at the point where the user needs space to be able to sit at the proper depth in their chair.

Many users of this brace are children born with Spina Bifida. This congenital disease often leaves a scarred lesion that is sensitive to pressure and friction. The central pivot point of the above-mentioned device, often lines up directly with this lesion. Fitting this device over a sensitive lesion can be extremely difficult since the central pivot post actually extends into the padded liner on the inside of the device.

Another disadvantage of the central pivot design is that it cannot be adjusted for growth. When the growing child no longer fits within the pelvic section of the device, a new device must be ordered. Not only is replacement expensive, but it can also leave the user without a device for a significant amount of time. This lost time not only restricts the users mobility, but it also allows muscular contractures to occur which adversly affect the rehabilitation process.

Standing balance in the above-mentioned device is established by adjusting the hip-flexion angle. Compared to the cable system, the central pivot system is easier to adjust but it still requires the user to remove the brace each time an adjustment needs to be made.

OBJECTS AND ADVANTAGES

Accordingly, several objects and advantages of my invention are as follows.

With two laterally located pivot points, the torque on the pivot points is greatly diminished because of the shorter distance between the pivot points and the hip joints. This decreased torque allows for the use of smaller and lighter materials. Since the user of this brace relies on upper body strength to transfer their weight, it is crucial that my invention be as light as possible.

The two laterally located pivot points also diminish the bulk of my invention thereby providing the user with more room to fit into existing seating systems.

Another advantage of the lateral pivot points is that adjustments can be made to the central area of the device where there is often a sensitive scarred-over lesion that must be protected from pressure or friction.

The width of my invention can also be adjusted as the user grows. By cutting the pelvic band through the middle, spreading the two sections apart, reconnecting the pelvic band at the wider dimension and finally adding a longer connecter bar, the device can be widened within two hours to fit the growing user. The savings for the beleagured health care industry that are realized by the growth adjustability of the present invention are significant. Replacement costs are not the only savings realized by the adjustability of the present invention.

The user of this type of brace easily develops soft tissue contractures around the knees and hips when not wearing the brace. Replacement can be a lengthy process during which time the user will be without a brace that fits. Once the new brace is fitted, it is often necessary for the user to undergo a costly and time-consuming course of physical therapy to regain the competence level present before the brace was outgrown.

Standing balance in the present invention can be adjusted easily and quickly while the use is in the brace. This andvantage saves fitting time and allows for more accurate adjustment of the users balance.

LIST OF REFERENCE NUMERALS

1. HIP JOINT ASSEMBLY
2. TIE-ROD/HIP JOINT ASSEMBLY
3. PELVIC BAND
3a. THREADED HOLE FOR PIVOT JOINT
4. TORSO SUPPORT
5. L-SHAPED PIVOT BAR
5a. PIVOT JOINT HOLE
5b. TIE-ROD/HIP JOINT ASSEMBLY HOLE
5c. TIE-ROD/CONNECTER BAR HOLE (THREADED)
6. PIVOT JOINT SCREW
6a. THRUST BEARING
6b. THRUST WASHER
6c. PIVOT JOINT NUT
6d. PIVOT JOINT SPACER

7. LEFT-THREADED TIE-ROD END
8. RIGHT-THREADED TIE-ROD END
9. CONNECTER BAR
10. SET SCREW
11. TIE-ROD ATTACHMENT SCREW

DESCRIPTION OF DRAWINGS

FIG. I is a left-side rear perspective view of a preferred embodiment of a hip-reciprocating apparatus made according to the present invention.

FIG. II is an exploded view of the pivot joint between the L-shaped pivot bar and the pelvic band. Also shown is an exploded perspective view of the joint between the L-shaped pivot bar and the connecter bar of the present invention.

DESCRIPTION OF INVENTION

Figure 1:
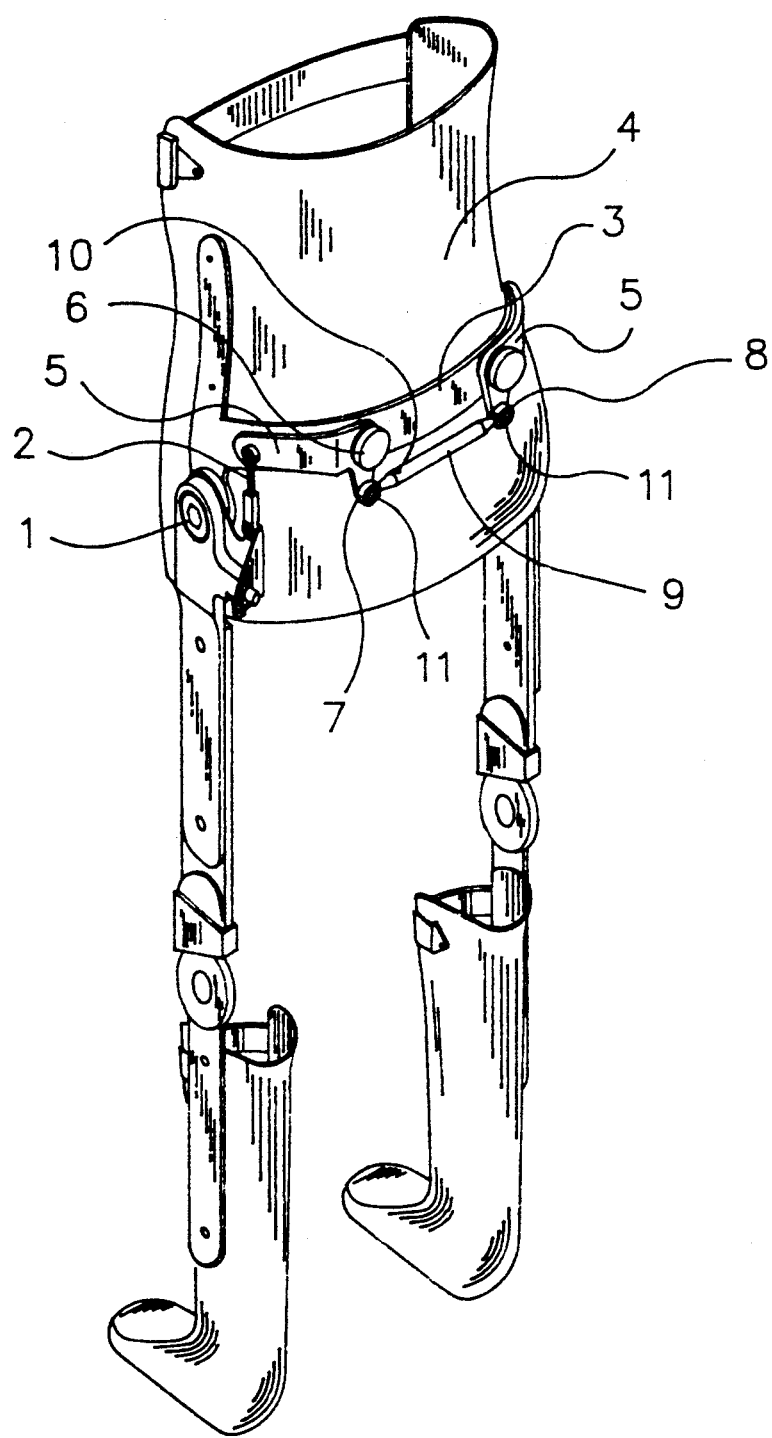
Figure 2:
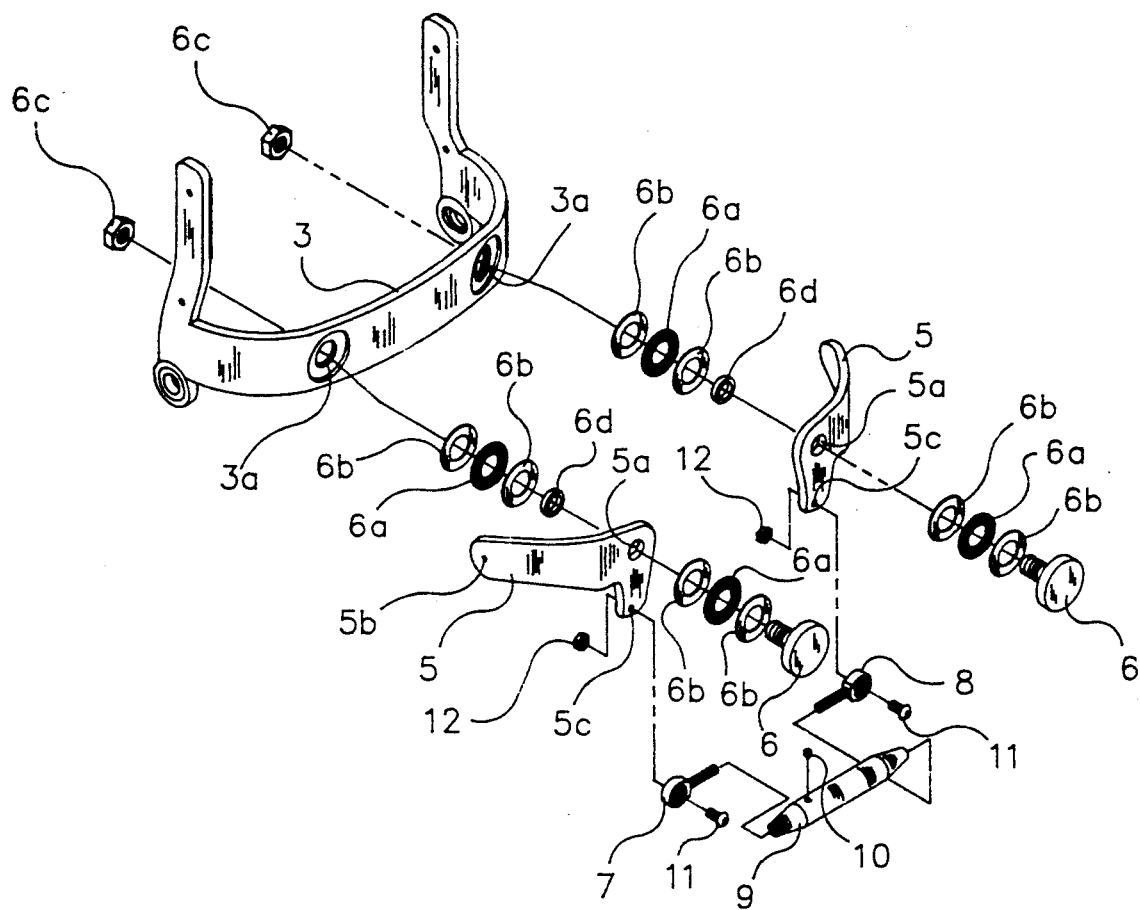

FIG. I shows a left-side rear perspective view of a hip-reciprocating apparatus with the present invention consisting of the mechanism in between the two tie-rod-/hip joint assemblies 2 and posterior to the torso support 4.

The attachment between the tie-rod/hip joint assembly 2 and the L-shaped pivot bar 5 is the same as described in my previous U.S. Pat. No. 4,964,628 to Poplawski, 1990 Oct. 23 page 3 lines 54 through 66. The hip joint assembly (1) is also described in my previous U.S. Pat. No. 4,964,628 to Poplawski, 1990 Oct. 23 page 3 lines 18 through 30.

In the present invention, only the left L-shaped pivot bar 5 will be described with the understanding that the right L-shaped pivot bar 5 is of equivalent description.

From the tie-rod/hip joint assembly hole 5b, the L-shaped pivot bar 5 follows the contour of the pelvic band 3 until arriving at the pivot joint hole 5a. As shown in FIG. II, pivot joint screw 6 passes through pivot joint hole 5a and threaded hole 3a. Pivot joint screw 6, thrust bearings 6a, thrust washers 6b, pivot joint spacer 6d and pivot joint nut 6c combine with the L-shaped pivot bar 5 and the pelvic band 3 to allow the L-shaped pivot bar 5 to pivot freely relative to the pelvic band 3.

The short leg of the L-shaped pivot bar 5 bends inward towards the torso support 4 in a way that does not impede the pivoting motion of the L-shaped pivot bar 5. The left-threaded tie-rod end 7 is attached to the short leg of the L-shaped pivot bar 5 through the tie-rod connecter bar hole (threaded) 5c. This attachment is made with the the tie-rod attachment screw 11 and the tie-rod attachment nut 12.

The connecter bar 9 is threaded on both ends. One end has a right hand thread and the other end has a left hand thread. The connecter bar 9 is threaded onto its corresponding left-thread tie-rod end 7. Set screw 10 passes through connecter bar 9 and presses against the threads of the left-thread tie-rod end 7 to prevent rotation of connecter bar 9. The other end of the connecter bar 9 screws onto the right-thread tie-rod end 8. From the right-thread tie-rod end 8 to the tie-rod/hip joint assembly 2 on the right side of the present invention, the description is identical to the preceding description of the present invention.

OPERATION OF INVENTION

The goal of the present invention is to provide a mechanism whereby a reciprocating motion of the lower extremities is permitted without compromising the necessary support of the bracing system.

With the brace locked in its upright position, the present invention allows one leg to move forward as the other leg moves back. As the left leg swings forward, the tie-rod/hip joint assembly 2 pulls the long leg of the left L-shaped pivot bar 5 down. As the L-shaped pivot bar 5 descends, it is forced to pivot in a counter-clockwise direction around the left pivot joint screw 6.

The two pivot joint screws 6 are placed equidistant from the center of the pelvic band 3. This results in symmetrical operation of the reciprocating motion. The location of the two pivot joint screws 6 is determined by two factors. The first factor being that lever arm between the long leg of the L-shaped pivot bar 5 and the pivot joint hole 5a wants to be as short as possible to reduce the torque on the pivot joint screw 6. The second factor determining the location of the pivot joint screws 6 is the necessity of keeping the connecter bar 9 in an unbent straight configuration. This is important for maintaining the strength of the connecter bar 9 when the lateral shifting forces described in the next paragraph are described.

As the left L-shaped pivot bar 5 pivots counter-clockwise around the pivot joint screw 6, a lateral shifting force is applied to the tie-rod ends 7,8 and the connecter bar 9. This force is then transferred to the right L-shaped pivot bar 5. The pivoting around the right pivot joint screw 6 also occurs in a counter-clockwise direction forcing the long leg of the right L-shaped pivot bar 5 in an upwards direction. This upward pull on the tie-rod/hip joint assembly 2 forces the right leg of the user in a backwards direction, thus creating the reciprocal motion necessary for the function of the present invention.

When fitting the present invention on the user, it is necessary to adjust the angle between the torso section 4 and the leg sections. This adjustment provides the user with the most comfortable standing balance. In order to establish this balance, the set screw 10 is loosened allowing the connecter bar 9 to turn. Clockwise rotation increases the angle between the torso support 4 and the leg sections. This adjustment will force the user to stand more erect thereby moving the balance point closer to the heels of the feet. Conversly, turning the connecter bar 9 in a counter-clockwise direction will decrease the angle between the torso support 4 and the leg sections. This adjustment will decrease the angle between the torso support 4 and the leg sections thereby moving the balance point closer to the balls of the feet. When optimal balance is achieved, the set screw 10 is tightened against the left-thread tie-rod end 7 locking the balance angle into the desired position. This adjustment is made while the user is in the brace, therby allowing for quick and accurate balance adjustment.

Widening the pelvic section 3 for the continued fit of the growing user can be successfully accomplished by an experienced technician in the field.

First the torso support 4 is removed from the pelvic section 3 of the present invention. The connecter bar 9 is removed and the pelvic band 3 is cut through the middle on a vertical axis. Another piece of aluminum of similar width and thickness to the pelvic band 3 is riveted to the two halves of the pelvic band 3, reconnecting the brace to its former configuration but at a wider dimension. This new dimension is calculated to correspond to the larger trocanter to trocanter dimension of the user.

The connecter bar 9 must be replaced by a longer one to maintain the configuration of the present invention.

The torso support 4 must also be widened to fit the new dimension. In the preferred embodiment of the present invention, the torso support is made of a thermo-plastic that can be heated and adjusted into the wider dimension.

Finally, the torso support 4 is re-attached to the pelvic section 3, standing balance is adjusted and the brace is ready for continued use.

CONCLUSION, RAMIFICATIONS AND SCOPE OF INVENTION

Thus the reader will see that the orthopedic bracing mechanism for facilitating hip reciprocation of the invention provides a durable, economical, lightweight and highly adjustable device that can be successfully used for a long period of time.

While the above description contains many specifities, these should not be construed as limitations on the scope of the invention, but rather as an exemplification of one preferred embodiment thereof. For example, the shape of the L-shaped pivot bar illustrated could be altered without affecting function. Lighter, stronger materials may become available and economical, reducing further the weight and bulk of the brace.

Accordingly, the scope of the invention should be determined not by the embodiments illustrated, but by the appended claims and their legal equivalents.

I claim:

1. An apparatus positionable adjacent to the hips of a human body for facilitating walking and standing balance comprising: torso support having a pelvic band contoured around said torso support and both being contoured for surrounding the posterior aspect of the human torso, said pelvic band attached on each lateral side to a hip joint assembly and said pelvic band having a longitudinal axis along its contour; two identical L-shaped pivot bars of unitary singular construction pivotally mounted on the pelvic band, the long arms of the L-shaped pivot bars aligned along said longitudinal axis of the pelvic band extending adjacent to the hip joint assemblies and the short arms of the L-shaped pivot bars descending below the pelvic band; an adjustable connector bar pivotally attached to and connecting the short arms of the L-shaped pivot bars; linkage means for coupling the long arms of the L-shaped pivot bars with the hip joint assemblies, whereby the long arms of the L-shaped pivot bars move in opposite directions when each of said hip joint assemblies rotate around an axis on said torso support.

2. An apparatus according to claim 1 wherein the two L-shaped pivot bars each pivot about an axis disposed equidistant from the center of the pelvic section.

* * * * *